[19] United States Patent
Nakanishi et al.

[11] 3,978,071
[45] Aug. 31, 1976

[54] SUBSTITUTED PHENYLALKANOIC ACIDS AND DERIVATIVES

[75] Inventors: Michio Nakanishi; Tomio Muro, both of Nakatsu; Tohru Nakao; Kiyoshi Ogawa, both of Yoshitomi, all of Japan

[73] Assignee: Yoshitomi Pharmaceutical Industries, Ltd., Osaka, Japan

[22] Filed: July 8, 1974

[21] Appl. No.: 486,728

[30] Foreign Application Priority Data

| July 7, 1973 | Japan | 48-76944 |
| July 21, 1973 | Japan | 48-81380 |
| Sept. 13, 1973 | Japan | 48-104094 |
| Mar. 22, 1974 | Japan | 49-32898 |
| Mar. 27, 1974 | Japan | 49-35007 |

[52] U.S. Cl. .................. 260/295 K; 260/294.8 C; 260/294.9; 260/295 F; 260/247.1 L; 260/247.2 A; 260/268 BC; 260/326.43; 260/302 F; 260/256.4 F; 260/247.1 H; 424/251; 424/248; 424/256; 424/270; 424/250; 424/274; 424/275; 424/273; 424/267; 260/247.2 B; 260/293.6; 260/293.57; 260/306.8 F; 260/256.5 R; 260/247.5 DP; 260/247.5 F

[51] Int. Cl.² ........................................ C07D 471/04

[58] Field of Search .......... 260/294.8 C, 294.9, 260/295 K, 295 F, 247.1 L, 247.2 A, 268 BC, 293.59, 326.43, 247.2 B, 293.6

[56] References Cited
UNITED STATES PATENTS 3,318,880  5/1967  Almirante et al. ............ 260/294.8 C

*Primary Examiner*—Natalie Trousof
*Assistant Examiner*—Robert T. Bond
*Attorney, Agent, or Firm*—Sughrue, Rothwell, Mion, Zinn and Macpeak

[57] ABSTRACT

Substituted phenylalkanoic acids and derivatives thereof of the formula:

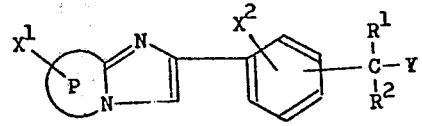

wherein each of $R^1$ and $R^2$ is a hydrogen atom or an alkyl group having 1 to 4 carbon atoms; each of $X^1$ and $X^2$ is a hydrogen atom, a halogen atom, an alkyl group having 1 to 4 carbon atoms or an alkoxy group having 1 to 4 carbon atoms; Y is COOH, COOR (wherein R is an alkyl group having 1 to 4 carbon atoms), $CONH_2$, $CSNH_2$, CN or COZ—A—N($R^3$)($R^4$) (wherein Z is an oxygen atom or an imino group, A is an alkylene group having 2 to 4 carbon atoms and each of $R^3$ and $R^4$ is a hydrogen atom or an alkyl group having 1 to 4 carbon atoms, or $R^3$ and $R^4$ together with the adjacent nitrogen atom form a saturated heterocycle selected from pyrrolidine, piperidine, morpholine, piperazine and piperazine substituted by an alkyl group having 1 to 4 carbon atoms at the 4-position; and ring P represents a pyridine ring, a pyrimidine ring or a thiazole ring; and pharmaceutically acceptable salts thereof are useful as analgesics, anti-pyrestics and anti-inflammatory agents.

8 Claims, No Drawings

SUBSTITUTED PHENYLALKANOIC ACIDS AND DERIVATIVES

This invention relates to novel and therapeutically valuable compounds of the formula:

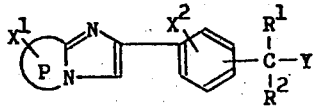   [I]

and pharmaceutically acceptable salts thereof, wherein each of $R^1$ and $R^2$ is a hydrogen atom or an alkyl group having 1 to 4 carbon atoms; each of $X^1$ and $X^2$ is a hydrogen atom, a halogen atom, an alkyl group having 1 to 4 carbon atoms or an alkoxy group having 1 to 4 carbon atoms; Y is COOH, COOR (wherein R is an alkyl group having 1 to 4 carbon atoms), $CONH_2$, $CSNH_2$, CN or COZ—A—$N(R^3)(R^4)$ (wherein Z is an oxygen atom or an imino group NH, A is an alkylene group having 2 to 4 carbon atoms and each of $R^3$ and $R^4$ is a hydrogen atom or an alkyl group having 1 to 4 carbon atoms, or $R^3$ and $R^4$ together with the adjacent nitrogen atom form a saturated heterocycle selected from pyrrolidine, piperidine, morpholine, piperazine and piperazine substituted by an alkyl group having 1 to 4 carbon atoms at the 4-position; and ring P represents a pyridine ring, a pyrimidine ring or a thiazole ring.

In the above definition, the alkyl group includes methyl, ethyl, propyl, isopropyl, butyl, isobutyl, sec-butyl and t-butyl; the alkoxy group includes methoxy, ethoxy, propoxy, isopropoxy, butoxy and isobutoxy; the alkylene group includes ethylene, trimethylene, propylene and tetramethylene; and the halogen atom includes F, Cl and Br.

The ring system:

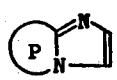

in the above formula [I] and also hereinafter represents any of the following structures (1)–(3).

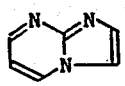 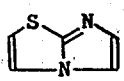

(1)     (2)     (3)

The compounds of formula [I] can be produced, for example, by the following methods:

I. In the case of compounds of formula [I] wherein Y is COOH, COOR, $CONH_2$, $CSNH_2$ or CN;
  a. By reacting a compound of the formula:

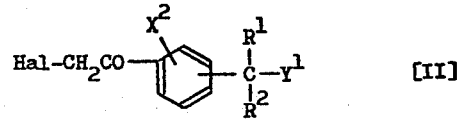   [II]

wherein $R^1$, $R^2$ and $X^2$ are as defined above, $Y^1$ is COOH, COOR (R being as defined above), $CONH_2$, $CSNH_2$ or CN, and Hal is a halogen atom (e.g. Cl or Br), with a compound of the formula:

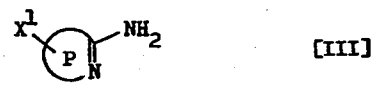   [III]

wherein each symbol is as defined above, the amino group being at 2-position of the ring P.

The reaction is usually carried out in an alcoholic solvent (e.g. methanol, ethanol or propanol) a 0°–150°C.

b. By reacting a compound of the formula:

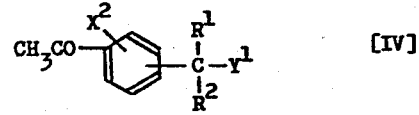   [IV]

wherein each symbol is as defined above, with iodine and a compound of formula [III].

The reaction is usually carried out in an alcoholic solvent (e.g. methanol, ethanol or propanol) at 0°–150°C.

c. By hydrolyzing a compound of the formula:

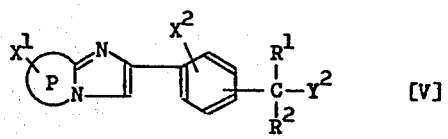   [V]

wherein $R^1$, $R^2$, $X^1$, $X^2$ and ring P are as defined above, and $Y^2$ is a functional group hydrolyzable to COOH [e.g. COOR' (wherein R' is an alkyl group having 1 to 4 carbon atoms such as methyl, ethyl, propyl or butyl, an aralkyl group such as benzyl or phenethyl or an aryl group such as phenyl), $CONH_2$,

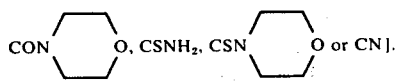

The hydrolysis is usually carried out in a solvent (e.g. water, acetic acid, methanol, ethanol, propanol, butanol, dimethylformamide, dimethyl sulfoxide or a mixture thereof) under acid conditions with hydrochloric acid, hydrobromic acid, hydriodic acid, hydrofluoric acid, sulfuric acid, nitric acid or phosphoric acid or basic conditions with lithium hydroxide, potassium hydroxide, sodium hydroxide, calcium hydroxide or barium hydroxide, at 0°–150°C.

According to this method (c), compounds of formula [I] wherein Y is COOH are obtained.

II. In the case of compounds of formula [I] wherein Y is $COZ-A-N(R^3)(R^4)$;

d. By reacting a compound of the formula:

[VI]

wherein A, $R^3$ and $R^4$ are as defined above, and Q is $NH_2$, OH, or a halogen atom (e.g. Cl or Br) or an alkyl- or aryl-sulfonyloxy (e.g. p-tolylsulfonyloxy or methylsulfonyloxy), with a compound of formula [I] wherein Y is COOH or its reactive derivative appropriately selected.

The reactive derivative of the compound of formula [I] wherein Y is COOH is, for example, a metal salt (e.g. sodium salt, potassium salt, calcium salt or silver salt), an acid halide (e.g. acid chloride) or a lower alkyl ester (e.g. methyl ester, ethyl ester, propyl ester or isopropyl ester).

The reaction is carried out in a conventional manner. For example, in the case of the reaction of the comound of formula [I] wherein Y is COOH or its metal salt with the compound of formula [VI] wherein Q is a halogen atom or an alkyl- or aryl-sulfonyloxy, the reaction is carried out with or without a solvent (e.g. methanol, ethanol, propanol, ethyl ether, tetrahydrofuran, dioxane, benzene, toluene, xylene, dimethylformamide, dimethyl sulfoxide or dimethylacetamide) at 10°–150°C; more particularly, the reaction is advantageously carried out by the use of sodium salt of the compound of formula [I] wherein Y is COOH and the compound of formula [VI] wherein Q is a halogen atom in dimethylformamide at 80°–90°C for 20–25 hours.

The compounds of formula [I] can be converted in a conventional manner into the acid addition salts with various inorganic or organic acids such as hydrochloric, hydrobromic, hydriodic, hydrofluoric, sulfuric, nitric, phosphoric, malonic, maleic, fumaric and oxalic acids. The compounds of formula [I] wherein Y is COOH can alternatively be converted in a conventional manner into the corresponding metal salts (the metal being for example Na, K, Ca, Mg or Al), the corresponding ammonium salts or the corresponding addition salts with organic bases such as diethylamine, diisopropylamine, morpholine and piperazine.

The compounds of formula [I] wherein $R^1$ and $R^2$ are different each other optically active compounds or racemic compounds. The racemic compounds can be separated in a conventional manner into two enantiomers.

The compounds of formula [I] and pharmaceutically acceptable salts thereof have analgesic and anti-inflammatory actions as shown, for example, by the following tests; in which the alphabetical notations A to E mean the following compounds, respectively:

A: 2-[4-(imidazo[1,2-a]pyridin-2-yl)phenyl]propionic acid,
B: 2-[3-chloro-4-(imidazo[1,2-a]pyridin-2-yl)phenyl]propionic acid,
C: 2-[3-fluoro-4-(imidazo[1,2-a]pyridin-2-yl)phenyl]propionic acid,
D: 2-[4-(imidazo[2,1-b]thiazol-6-yl)phenyl]propionic acid,
E: 2-[3-chloro-4-(imidazo[2,1-b]thiazol-6-yl)phenyl]propionic acid.

Analgesic Action (Phenylquinone Method)

According to the method of Hendershot et al. (J. Pharmacol. Exptl. Therap., 125, 237 (1959)), to one group of 6 dd-strain male mice each weighing about 20 g a test solution containing a test compound was orally administered and 1 hour later 0.2 ml/20 g of body weight of 0.02% o-phenyl-p-benzoquinone solution was intraperitoneally injected. The frequency of stretch symptoms thus induced was measured for 30 minutes, and compared with that of a control group, and the inhibition percentage (effect) was calculated. The $ED_{50}$, the dose required for 50% inhibition, was calculated from the dose-response curve.

Anti-inflammatory Action i. Carrageenin Edema Method

According to the method of Winter et al. (Proc. Soc. Exptl. Biol. Med., 111, 544 (1962)), to one group of 5 Donryu-strain male rats each weighing about 130 g a test solution containing a test compound was administered orally. One hour later 0.05 ml of 1% carrageenin solution as phlogogenic substance was subcutaneously injected to the paw of the hind leg. And 2 hours after the administration of phlogogen the bulk of the paw was measured in order to obtain the increment percentage over that before administration. The ratio of bulk increment between a control group and a test group was calculated as inhibition percentage. The $ED_{50}$, the dose required for 50% inhibition, was calculated from the dose-response curve.

ii. Ultraviolet Erythema Method:

Using guinea pigs weighing 250–450 g, a rubber plate with 3 holes of 7 mm in diameter was fitted to the abdomen, hair of which had been removed in advance, and light was given by a mercury lamp (300 W) at the distance of 15 cm for 150 seconds. Two hours later the degree of erythema formation was marked according to the method of Winder et al. (Arch. Intern. Pharmacodyn., 116, 261 (1958); 1 for distinct erythema, 0.5 for indistinct erythema and 0 for no erythema) and the efficacy rate was calculated, based on the criterion that 1.5 or less of total marks be effective. Equal amounts of the test solution were orally given 1 hour before and after the irradiation, respectively. The $ED_{50}$, the total dose required for 50% efficacy rate, was calculated from the dose-response curve.

Results:

Table I

| Compounds | ED$_{50}$ (mg/kg) p.o. | | |
|---|---|---|---|
| | Phenylquinone | Carrageenin Edema | Ultraviolet Erythema |
| A | 0.1 | 8.0 | 6 |
| B | 0.2 | 25 | 1 |
| C | 0.1 | 25 | 2.5 |
| D | 13 | 50 | 2.5 |
| E | 0.5–1 | 100 | 5 |

In view of various tests including those mentioned above, the compounds of formula [I] in accordance with the invention and pharmaceutically acceptable salts thereof can be administered safely as analgesics, antipyretics and anti-inflammatory agents, either alone or in the form of a pharmaceutical composition consisting essentially of a therapeutically effective amount of the compound in admixture with a suitable and conventional carrier or adjuvent, administrable orally, percutaneously or by way of injection, without harm to the host.

The pharmaceutical composition can take the form of tablets, granules, powder or capsules, for oral administration, of injectable solution for subcutaneous or intramuscular administration, or of cream, ointment, jelly or suppository for topical administration. The choice of carrier is determined by the preferred form of administration, the solubility of the compounds and standard pharmaceutical practice.

The following is an example of formulations when a compound of the invention is administered for pharmaceutical purposes:

25 mg tablets are prepared from the following composition:

| | |
|---|---|
| Compound [A] | 25. mg |
| Lactose | 44 |
| Corn starch | 28 |
| Microcrrystalline cellulose | 20 |
| Methyl cellulose | 0.9 |
| Talc | 2 |
| Magnesium stearate | 0.9 |
| | 120.8 mg |

0.5% injectable solution is prepared from the following composition:

| | |
|---|---|
| Compound [A] | 0.5% |
| Sodium chloride | 0.9 |
| Distilled water | 98.6 |
| | 100.0% |

The usual daily dose of compound [I] or a salt thereof lies in the range of about 50–150 milligrams per human adult.

The present invention is further explained by way of the following illustrative examples.

EXAMPLE 1

A mixture of 96 g of ethyl 4-(chloroacetyl)phenylacetate, 200 ml of ethanol and 64 g of 2-aminopyridine is heated under reflux for 2 hours. The ethanol is distilled off under reduced pressure, and water is added to the residue. The mixture is extracted with benzene, and the extract is washed with water, dried and concentrated to give a brown oil. To the oil is added ether, and the crystalline precipitate is filtered off and recrystallized from a mixture of benzene and petroleum ether to give 44 g of ethyl 4-(imidazo[1,2-a]pyridin-2-yl)phenylacetate as pale brown crystals melting at 92°–93°C.

EXAMPLE 2

A mixture of 47 g of ethyl 2-[4-(chloroacetyl)-phenyl]propionate, 100 ml of ethanol and 30 g of 2-aminopyridine is heated under reflux for 2 hours. The ethanol is distilled off under reduced pressure, and water is added to the residue. The mixture is extracted with benzene, and the extract is washed with water, dried and concentrated to give a reddish brown oil. To the oil is added isopropyl ether, and the crystalline precipitate is filtered off and recrystallized from isopropyl ether to give 22 g of ethyl 2-[4-(imidazo[1,2-a]pyridin-2-yl)phenyl]propionate as colorless scales melting at 110°–112°C.

EXAMPLE 3

A mixture of 48 g of ethyl 4-(chloroacetyl)phenylacetate, 100 ml of ethanol and 38 g of 2-aminopyrimidine is heated under reflux for 3 hours. The ethanol is distilled off under reduced pressure, and water is added to the residue. The mixture is extracted with ethyl acetate, and the extract is washed with water, dried and concentrated to give a brown oil. To the oil is added benzene, and the crystalline precipitate is filtered off and recrystallized from ethyl acetate to give 26 g of ethyl 4-(imidazo[1,2-a]-pyrimidine-2-yl)phenylacetate as pale brown crystals melting at 155°–158°C.

EXAMPLE 4

A mixture of 25.5 g of ethyl 2-[4-(chloroacetyl)-phenyl]propionate, 50 ml of ethanol and 19 g of 2-aminopyrimidine is heated under reflux for 3 hours. The ethanol is distilled off under reduced pressure, and water is added to the residue. The mixture is extracted with ethyl acetate, and the extract is washed with water, dried and concentrated to give a reddish brown oil. To the oil are added ethyl acetate and isopropyl ether, and the crystalline precipitate is filtered off and recrystallized from ethanol to give 8.4 g of ethyl 2-[4-(imidazo[1,2-a]pyrimidin-2-yl)phenyl]propionate as colorless scales melting at 171°–173°C.

EXAMPLE 5

A mixture of 38 g of ethyl 4-(chloroacetyl)phenylacetate, 60 ml of ethanol and 32 g of 2-aminothiazole is heated under reflux for 2 hours. The ethanol is distilled off under reduced pressure, and water is added to the residue. The mixture is extracted with benzene, and the extract is washed with water, dried and concentrated. To the residual reddish brown oil are added benzene and isopropyl ether, and the crystalline precipitate is filtered off and recrystallized from ethanol to give 14 g of ethyl 4-(imidazo[2,1-b]-thiazol-6-yl)phenylacetate as colorless crystals melting at 117°–119°C.

EXAMPLE 6

A mixture of 28 g of 4-(chloroacetyl)phenylacetonitrile, 70 ml of ethanol and 24 g of 2-aminopyridine is heated under reflux for 2 hours. The ethanol is distilled off under reduced pressure, and water is added to the residue. The crystalline precipitate is filtered off and recrystallized from methanol to give 21 g of 4-(imidazo[1,2-a]pyridin-2-yl)phenylacetonitrile as colorless crystals melting at 175°–177°C with decomposition.

EXAMPLE 7

A mixture of 9 g of 2-[4-(chloroacetyl)phenyl]propionamide, 30 ml of ethanol and 7.6 g of 2-aminopyridine is heated under reflux for 2 hours. The ethanol is distilled off under reduced pressure, and water is added to the residue. The crystalline precipitate is filtered off and recrystallized from aqueous dimethylformamide to give 6.9 g of 2-[4-(imidazo[1,2-a]pyridin-2-yl)phenyl]-propionamide as colorless scales melting at 219°–220°C.

EXAMPLE 8

A mixture of 6 g of ethyl 4-acetylphenylacetate, 20 ml of ethanol, 7.5 g of iodine and 5.7 g of 2-aminopyridine is heated under reflux for 3 hours. The ethanol is distilled off under reduced pressure, and the residue is extracted with ethyl acetate. The extract is washed with water, dried, and concentrated to give a reddish brown oil. The oil is column chromatographed over silica gel with chloroform as eluent, and the colorless crystals obtained from the chloroform eluate are recrystallized from a mixture of benzene and petroleum ether to give 3.0 g of ethyl 4-(imidazo[1,2-a]pyridin-2-yl)phenylacetate melting at 92°–93°C.

EXAMPLE 9

A mixture of 5.2 g of ethyl 4-(imidazo[1,2-a]pyridin-2-yl)phenylacetate, 20 ml of ethanol, 0.96 g of sodium hydroxide and 5 ml of water is stirred at room temperature for 10 minutes. The ethanol is distilled off under reduced pressure, and the residue is dissolved in water. The solution is adjusted to pH 6 by addition of dilute hydrochloric acid. The crystalline precipitate is filtered off, washed with water, and recrystallized from ethanol to give 2.3 g of 4-(imidazo[1,2-a]pyridin-2-yl)phenylacetic acid as colorless crystals melting at 217°–221°C with decomposition.

EXAMPLE 10

A mixture of 8 g of ethyl 2-[4-(imidazo[1,2-a]pyridin-2-yl)phenyl]-propionate, 50 ml of ethanol, 1.4 g of sodium hydroxide and 10 ml of water is heated under reflux for 2 hours. The ethanol is distilled off under reduced pressure, and the residue is dissolved in water. The solution is adjusted to pH 6 by addition of dilute hydrochloric acid. The crystalline precipitate is filtered off, washed with water, and recrystallized from methanol to give 4 g of 2-[4-(imidazo[1,2-a]pyridin-2-yl)phenyl]propionic acid as colorless crystals melting at 244°–246°C with decomposition. The corresponding hydrochloride melts at 210°–211°C.

EXAMPLE 11

A mixture of 6 g of ethyl 4-(imidazo[1,2-a]pyrimidin-2-yl)phenyl-acetate, 30 ml of ethanol, 1.1 g of sodium hydroxide and 5 ml of water is stirred at room temperature for 10 minutes. The crystalline precipitate is filtered off, washed with ethanol, and then dissolved in water. The solution is adjusted to pH 6 by addition of dilute hydrochloric acid. The crystalline precipitate is filtered off and washed with water to give 3.2 g of 4-(imidazo-[1,2-a]pyrimidin-2-yl)phenylacetic acid as colorless crystals melting at 264°–265°C with decomposition.

EXAMPLE 12

A mixture of 4.4 g of ethyl 2-[4-(imidazo[1,2-a]pyrimidin-2-yl)-phenyl]propionate, 50 ml of ethanol, 0.72 g of sodium hydroxide and 5 ml of water is heated under reflux for 2 hours. The ethanol is distilled off, and acetone is added to the residue. The crystalline precipitate is dissolved in water, and the solution is adjusted to pH 6 by addition of dilute hydrochloric acid. The crystalline precipitate is filtered off and washed with water to give 2.8 g of 2-[4-(imidazo[1,2-a]pyrimidin-2yl)phenyl]propionic acid as colorless crystals melting at 248°C with decomposition.

EXAMPLE 13

A mixture of 5.7 g of ethyl 4-(imidazo[2,1-b]thiazol-6-yl)phenyl-acetate, 25 ml of ethanol, 0.96 g of sodium hydroxide and 5 ml of water is stirred at room temperature for 10 minutes. The ethanol is distilled off under reduced pressure, and the residue is dissolved in water. The solution is adjusted to pH 6 by addition of dilute hydrochloric acid. The crystalline precipitate is filtered off and washed with water to give 2.9 g of 4-(imidazo[2,1-b]thiazol-6-yl)phenylacetic acid as colorless crystals melting at 248°–249°C with decomposition.

EXAMPLE 14

A mixture of 2 g of 4-(imidazo[1,2-a]pyridin-2-yl)phenylacetonitrile, 10 ml of glacial acetic acid and 10 ml of concentrated hydrochloric acid is heated under reflux for 1 hour. The solvent is distilled off under reduced pressure, and water is added to the residue. The mixture is alkalified with 10% sodium hydroxide, and then filtered. The filtrate is adjusted to pH 6 by addition of 10% hydrochloric acid. The crystalline precipitate is filtered off and washed with water to give 1.2 g of 4-(imidazo[1,2-a]-pyridin-2-yl)phenylacetic acid as colorless crystals melting at 220°–222°C with decomposition.

EXAMPLE 15

A mixture of 1 g of 4-(imidazo[1,2-a]pyridin-2-yl)phenylacetamide, 5 ml of glacial acetic acid and 5 ml of concentrated hydrochloric acid is heated under reflux for 1 hour. The solvent is distilled off under reduced pressure, and water is added to the residue. The mixture is alkalified with 10% sodium hydroxide, and then filtered. The filtrate is adjusted to pH 6 by addition of 10% hydrochloric acid. The crystalline precipitate is filtered off and washed with water to give 0.8 g of 4-(imidazo[1,2-a]pyridin-2-yl)phenylacetic acid as colorless crystals melting at 220°–222°C with decomposition.

EXAMPLE 16

A mixture of 0.9 g of 4-(imidazo[1,2-a]pyridin-2-yl)phenylaceto-thiomorpholide, 20 ml of ethanol and 20 ml of 2N sodium hydroxide is heated under reflux for 5 hours. The ethanol is distilled off, and the residue is dissolved in water. The solution is adjusted to pH 5 by addition of hydrochloric acid. The crystalline precipitate is filtered off and washed with water to give 0.3 g of 4-(imidazo[1,2-a]pyridin-2-yl)phenylacetic acid as pale yellow crystals melting at 217°–221°C with decomposition.

The starting compound, 4-(imidazo[1,2-a]pyridin-2-yl)phenylaceto-thiomorpholide can be produced, for example, as follows:

A solution of methylmagnesium iodide (prepared from 3.6 g of magnesium and 22 g of methyl iodide) in 40 ml of ether is added dropwise to a mixture of 6.5 g of 4-(imidazo[1,2-a]pyridin-2-yl)benzonitrile and 50 ml of tetrahydrofuran with stirring on an ice bath. The mixture is heated under reflux for 3 hours, and the reaction mixture is cooled with salt and ice. 100 ml of 50% sulfuric acid is added dropwise to the reaction mixture, water is added, and the whole mixture is adjusted to pH 8 by addition of 20% sodium hydroxide. The crystalline precipitate is filtered off, washed with water and recrystallized from dimethylformamide to give 4.2 g of 2-(4-acetylphenyl)-imidazo[1,2-a]pyridine as colorless crystals melting at 209°–210°C. 2.2 g of the thus-obtained 2-(4-acetylphenyl)-imidazo[1,2-a]pyridine is heated with 0.45 g of sulfur and 10 ml of morpholine under reflux for 6 hours. The reaction mixture is cooled, and ethanol is added. The crystalline precipitate is filtered off and washed with ethanol to give 1.4 g of 4-(imidazo[1,2-a]pyridin-2-yl)phenylacetothiomorpholide as yellowish brown crystals melting at 204°–206°C.

EXAMPLE 17

4.2 g of p-toluenesulfonyl chloride is added to a mixture of 5.3 g of 2-[4-(imidazo[1,2-a]pyridin-2-yl)phenyl]propionic acid, 2.0 g of 2-dimethyl-aminoethanol and 50 ml of pyridine under cooling. The whole mixture is stirred for 30 minutes at room temperature, and further stirred at 70°–80°C for 5 hours. The reaction mixture is poured into water, and extracted with chloroform. The extract is washed with water, dried over magnesium sulfate and concentrated under reduced pressure. The residue is dissolved in ethyl acetate, and to the solution is added 3 ml of methyl iodide. The mixture is heated, and then allowed to stand at room temperature. The precipitate is filtered off and recrystallized from a mixture of ethanol and isopropyl ether to give 3.0 g of 2-dimethylaminoethyl 2-[4-(imidazo[1,2-a]pyridin-2-yl)phenyl]propionate methiodide monohydrate melting at 183°–185°C.

EXAMPLE 18

A mixture of 5.3 g of 2-[4-(imidazo[1,2-a]pyridin-2-yl)phenyl]-propionic acid, 100 ml of dimethylformamide and 1 g of 50% sodium hydride is stirred for 30 minutes, and 4 g of 2-dimethylaminoethyl chloride is added to the mixture. The whole mixture is allowed to stand at 80°–90°C for 20 hours. The reaction mixture is concentrated under reduced pressure, and the residue is extracted with 200 ml of chloroform. The extract is washed with water, dried over magnesium sulfate and concentrated under reduced pressure. The residue is dissolved in ethyl acetate, and 3 ml of methyl iodide is added to the solution. The mixture is heated, and then allowed to stand at room temperature. The precipitate is filtered off and recrystallized from a mixture of ethanol and isopropyl ether to give 3.0 g of 2-dimethylaminoethyl 2-[4-(imidazo[1,2-a]pyridin-2-yl)phenyl]-propionate methiodide monohydrate melting at 183°–185°C.

EXAMPLE 19

A small amount of p-toluenesulfonic acid monohydrate is added to a mixture of 5.3 g of 2-[4-imidazo[1,2-a]pyridin-2-yl)phenyl]propionic acid, 2.6 g of N,N-dimethylethylenediamine and 100 ml of xylene. The whole mixture is stirred under reflux for 5 hours, while the water produced is removed. The reaction mixture is cooled, and the crystalline precipitate is filtered off, washed with aqueous sodium bicarbonate solution and water, and recrystallized from toluene to give 4.0 g of N-(2-dimethylaminoethyl)-2-[4-(imidazo[1,2-a]pyridin-2-yl)phenyl]propionamide melting at 149°–150°C.

EXAMPLE 20

6.2 g of 2-[4-(imidazo[1,2-a]pyridin-2-yl)phenyl]-propionyl chloride, which is produced by treating 2-[4-(imidazo[1,2-a]pyridin-2-yl)phenyl]-propionic acid hydrochloride with thionyl chloride in chloroform, is added to a solution of 2.6 g of N,N-dimethylethylenediamine in 50 ml of pyridine. The mixture is allowed to stand at room temperature for 3 hours, and concentrated under reduced pressure. The residue is neutralized with aqueous sodium bicarbonate solution. The crystalline precipitate is washed with water and recrystallized from toluene to give 2.3 g of N-(2-dimethylamino-ethyl)-2-[4-(imidazo[1,2-a]pyridin-2-yl)phenyl]propionamide melting at 149°–150°C.

Using the procedure set forth in the above examples, but substituting equivalent amounts of appropriate starting materials, the following compounds are also produced:

1. 4-(6-chloro-imidazo[1,2-a]pyridin-2-yl)phenylacetic acid, melting at 263°–265°C with decomposition;
2. 4-(7-methyl-imidazo[1,2-a]pyridin-2-yl)phenylacetic acid, melting at 238°–242°C with decomposition;
3. 4-(7-methoxy-imidazo[1,2-a]pyridin-2-yl)phenylacetic acid;
4. 3-fluoro-4-(imidazo[1,2-a]pyridin-2-yl)phenylacetic acid, melting at 194°–196°C;
5. 3-(imidazo[1,2-a]pyridin-2-yl)-4-methylphenylacetic acid, melting at 187°–187.5°C;
6. 5-fluoro-2-(imidazo[1,2-a]pyridin-2-yl)phenylacetic acid, melting at 170°–173°C with decomposition;
7. 2-[4-(6-chloro-imidazo[1,2-a]pyridin-2-yl)phenyl]propionic acid, melting at 255°–256°C with decomposition;
8. 2-[3-fluoro-4-(imidazo[1,2-a]pyridin-2-yl)phenyl]propionic acid, melting at 210°–213°C with decomposition;
9. 2-[3-chloro-4-(imidazo[1,2-a]pyridin-2-yl)phenyl]propionic acid, melting at 208°–209°C with decomposition; the corresponding hydrochloride melting at 218°–219°C;
10. 2-[3-methoxy-4-(imidazo[1,2-a]pyridin-2-yl)phenyl]propionic acid;
11. 2-[2-(imidazo[1,2-a]pyridin-2-yl)phenyl]propionic acid, melting at 110°–111.5°C; the corresponding hydrochloride melting at 263°–265°C with decomposition;
12. 2-[5-fluoro-2-(imidazo[1,2-a]pyridin-2-yl)phenyl]propionic acid, melting at 155°–160°C;

13. 2-[5-chloro-2-(imidazo[1,2-a]pyridin-2-yl)phenyl]propionic acid, melting at 188°–189°C with decomposition;
14. 3-(imidazo[1,2-a]pyrimidin-2-yl)-4-methylphenylacetic acid ½ hydrate, melting at 219°–219.5°C;
15. 3-(imidazo[2,1-b]thiazol-6-yl)-4-methylphenylacetic acid, melting at 207°–208°C;
16. ethyl 4-(7-methyl-imidazo[1,2-a]pyridin-2-yl)phenylacetate, melting at 115°–117°C;
17. 4-(imidazo[1,2-a]pyridin-2-yl)phenylacetamide, melting at 252°–253°C with decomposition;
18. 2-[4-(6-chloro-imidazo[1,2-a]pyridin-2-yl)phenyl]propionamide, melting at 233°–234°C;
19. 2-[4-(7-methyl-imidazo[1,2-a]pyridin-2-yl)phenyl]propionamide, melting at 236°–239°C with decomposition;
20. 2-[4-(imidazo[2,1-b]thiazol-6-yl)phenyl]propionamide, melting at 226°–227°C;
21. 2-[4-(imidazo[1,2-a]pyrimidin-2-yl)phenyl]propionamide, melting at 248°–250°C with decomposition;
22. 4-(imidazo[1,2-a]pyridin-2-yl)phenylacetothioamide, melting at 172°–175°C with decomposition;
23. 2-[4-(imidazo[1,2-a]pyridin-2-yl)phenyl]propionitrile, melting at 124°–125°C;
24. 2-[4-(6-chloro-imidazo[1,2-a]pyridin-2-yl)phenyl]propionitrile, melting at 167°–168°C;
25. 2-[4-(imidazo[2,1-b]thiazol-6-yl)phenyl]propionitrile, melting at 159°–160°C;
26. 2-[4-(imidazo[1,2-a]pyrimidin-2-yl)phenyl]propionitrile, melting at 201°–202°C;
27. 2-piperidinoethyl 2-[4-(imidazo[1,2-a]pyridin-2-yl)phenyl]propionate dihydrochloride ½ hydrate, melting at 210°–211°C;
28. 2-(4-methyl-1-piperazinyl)ethyl 2-[4-(imidazo[1,2-a]pyridin-2-yl)-phenyl]propionate trimaleate, melting at 152.5°–153°C;
29. N-(2-dimethylaminoethyl)-2-[4-(7-methyl-imidazo[1,2-a]pyridin-2-yl)-phenyl]propionamide, melting at 157°–157.5°C;
30. N-(2-dimethylaminoethyl)-2-[4-(6-chloro-imidazo[1,2-a]pyridin-2-yl)-phenyl]propionamide, melting at 167.5°–169.5°C;
31. N-(2-dimethylaminoethyl)-2-[2-(imidazo[1,2-a]pyridin-2-yl)phenyl]-propionamide dimaleate, melting at 115°–117°C;
32. N-(2-dimethylaminoethyl)-2-[3-(imidazo[2,1-b]thiazol-6-yl)-4-methyl-phenyl]acetamide, melting at 135°–136°C;
33. N-(3-diethylaminopropyl)-2-[4-(imidazo[1,2-a]pyridin-2-yl)phenyl]-propionamide, melting at 119°C;
34. N-[2-(1-pyrrolidinyl)ethyl]-2-[4-(imidazo[1,2-a]pyridin-2-yl)phenyl]-propionamide; and
35. N-(2-morpholinoethyl)-2-[4-(imidazo[1,2-a]pyridin-2-yl)phenyl]-propionamide, melting at 159°–159.5°C;

As exemplified in Examples 17 and 18, the compounds of the present invention, when Y is CO-Z—A—N($R^3$)($R^4$) wherein Z is an oxygen atom or an imino group, A is an alkylene group having 2 to 4 carbon atoms and each of $R^3$ and $R^4$ is an alkyl group having 1 to 4 carbon atoms, or $R^3$ and $R^4$ together with the adjacent nitrogen atom form a saturated heterocycle selected from pyrrolidine, piperidine, morpholine, piperazine and piperazine substituted by an alkyl group having 1 to 4 carbon atoms at the 4-position, can form quaternary ammonium salts such as methiodide, ethiodide, ethobromide and methosulfate.

What is claimed is:
1. A member selected from the group consisting of a compound of the formula:

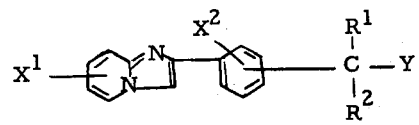

wherein each of $R^1$ and $R^2$ is a hydrogen atom or an alkyl group having 1 to 4 carbon atoms; each of $X^1$ and $X^2$ is a hydrogen atom, a halogen atom, an alkyl group having 1 to 4 carbon atoms or an alkoxy group having 1 to 4 carbon atoms; and Y is COOH, COOR (wherein R is an alkyl group having 1 to 4 carbon atoms), $CONH_2$, $CSNH_2$, CN or COZ—A—N($R^3$)($R^4$) (wherein Z is an oxygen atom or the group =NH, A is an alkylene group having 2 to 4 carbon atoms and each of $R^3$ and $R^4$ is a hydrogen atom or an alkyl group having 1 to 4 carbon atoms, or $R^3$ and $R^4$ together with the adjacent nitrogen atom form a saturated heterocycle selected from pyrrolidine, piperidine, morpholine, piperazine and piperazine substituted by an alkyl group having 1 to 4 carbon atoms at the 4-position.

2. A member selected from the group consisting of a compound of the formula:

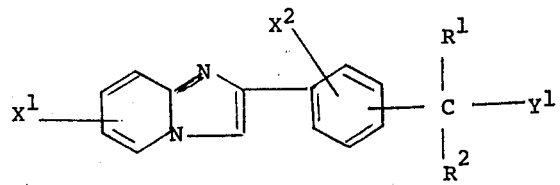

wherein each of $R^1$ and $R^2$ is a hydrogen atom or an alkyl group having 1 to 4 carbon atoms; each of $X^1$ and $X^2$ is a hydrogen atom, a halogen atom, an alkyl group having 1 to 4 carbon atoms or an alkoxy group having 1 to 4 carbon atoms; $Y^1$ is COOH, COOR (wherein R is an alkyl group having 1 to 4 carbon atoms), $CONH_2$, $CSNH_2$ or CN.

3. A member selected from the group consisting of a compound of the formula:

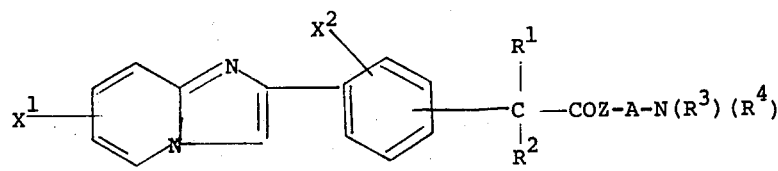

wherein each of $R^1$ and $R^2$ is a hydrogen atom or an alkyl group having 1 to 4 carbon atoms; each of $X^1$ and $X^2$ is a hydrogen atom, a halogen atom, an alkyl group having 1 to 4 carbon atoms or an alkoxy group having 1 to 4 carbon atoms; Z is an oxygen atom or the group =NH; A is an alkylene group having 2 to 4 carbon atoms; each of R³ and R⁴ is a hydrogen atom or an alkyl group having 1 to 4 carbon atoms, or R³ and R⁴ together with the adjacent nitrogen atom form a heterocycle selected from pyrrolidine, piperidine, morpholine, piperazine and piperazine substituted by an alkyl group having 1 to 4 carbon atoms at the 4-position.

4. A member selected from the group consisting of a compound of the formula:

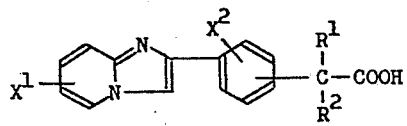

wherein each of R¹ and R² is a hydrogen atom or an alkyl group having 1 to 4 carbon atoms; and each of X¹ and X² is a hydrogen atom, a halogen atom, an alkyl group having 1 to 4 carbon atoms or an alkoxy group having 1 to 4 carbon atoms.

5. A compound of claim 1:
2-[4-(imidazo[1,2-a]pyridin-2-yl)phenyl]propionic acid.

6. A compound of claim 1:
2-[3-chloro-4-(imidazo[1,2-a]pyridin-2-yl)phenyl]-propionic acid.

7. A compound of claim 1:
2-[3-fluoro-4-(imidazo[1,2-a]pyridin-2-yl)phenyl]-propionic acid.

8. A compound of claim 1:
2-[4-(imidazo[1,2-a]pyridin-2-yl)phenyl]propionamide.

* * * * *